(12) United States Patent
Baxter et al.

(10) Patent No.: US 6,310,088 B1
(45) Date of Patent: Oct. 30, 2001

(54) HYDROXAMIC AND CARBOXYLIC ACID DERIVATIVES HAVING MMP AND TNF INHIBITORY ACTIVITY

(75) Inventors: Andrew Douglas Baxter; David Alan Owen; John Gary Montana; Elizabeth Jane Reed Nicholson, all of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/564,217

(22) Filed: May 4, 2000

Related U.S. Application Data

(63) Continuation of application No. 09/190,334, filed on Nov. 12, 1998, now abandoned.
(60) Provisional application No. 60/068,793, filed on Dec. 24, 1997.

(30) Foreign Application Priority Data

Nov. 12, 1997 (GB) .................................................. 9723904
Jun. 29, 1998 (GB) .................................................. 9814043

(51) Int. Cl.⁷ ........................ C07D 333/60; A01K 31/381
(52) U.S. Cl. ............................................. 514/443; 549/58
(58) Field of Search ................................ 549/58; 514/443

(56) References Cited

U.S. PATENT DOCUMENTS

| 3,558,655 | 1/1971 | Kaltenbronn . |
| 3,770,733 | 11/1973 | Sianesi . |
| 4,129,655 | 12/1978 | Huebner . |
| 4,224,330 | 9/1980 | Henrick et al. . |
| 4,297,369 | 10/1981 | Takizawa et al. . |

FOREIGN PATENT DOCUMENTS

| 0350163 | 1/1990 | (EP) . |
| 0483772 | 5/1992 | (EP) . |
| 52083543 | 12/1977 | (JP) . |
| 02250831 | 8/1990 | (JP) . |
| 9320047 | 10/1993 | (WO) . |
| 9743249 | 11/1997 | (WO) . |

OTHER PUBLICATIONS

Amyes, T.L., A.J. Kirby (1988) "Intramolecular Nucleophilic Addition of Phenolate Oxygen to Double Bonds Activated by Carboxyl and Carboxylate Groups. Relative Reactivity, Stereochemistry, and Mechanism." J. Am. Chem. Soc. 110:6505–6514.
Deorha, D.S. and Padma Gupta (1966) "The Synthesis of 3–t–Butyl–6–methyl–2–benzofurylacetic Acid" Notes 39(12):2768–2770.
Goldsmith, D.J. et al. (1973) "Aromatic Precursors in Trichothecene Synthesis. Addition of Lithioethyl Acetate to a Pyrylium Salt" Syn. Commun. 3(3):231–235 **Abstract No. 91904t/Chemical Abstracts vol. 79(15):412.
Dann, O. et al. (1982) "Synthesen Biskationishcher, Trypanocider 1–Benzofuran–Verbindungen" Liebigs Ann. Chem. pp. 1836–1869.
Descamps, M., E. Van Durme, M. Culot, and R. Charlier (Sep.–Oct. 1973) Chimie Therapeutique 5:536–544.

*Primary Examiner*—Robert Gerstl
(74) *Attorney, Agent, or Firm*—Saliwanchik, Lloyd & Saliwanchik

(57) ABSTRACT

Compounds of formula (I)

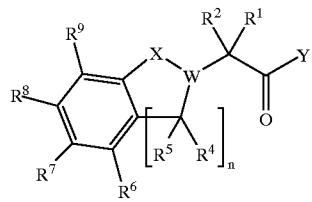

(I)

are useful therapeutic agents, by virtue of having MMP and TNF inhibitory activity.

60 Claims, No Drawings

HYDROXAMIC AND CARBOXYLIC ACID DERIVATIVES HAVING MMP AND TNF INHIBITORY ACTIVITY

CROSS-REFERENCE TO RELATED APPLICATIONS

This is a continuation of application Ser. No. 09/190,334, filed Nov. 12, 1998 now abandoned, which claims priority from provisional application U.S. Ser. No. 60/068,793, filed Dec. 24, 1997.

FIELD OF THE INVENTION

Metalloproteinases, including matrix metalloproteinases) MMPs), (human fibroblast) collagenase, gelatinase and TNF convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenases, stromelysins and gelatinases, have been shown to inhibit the release of TNF both in vitro and in vivo. See Gearing et al (1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNF are described in WO-A-9513289, WO-A-9611209, WO-A-96035687, WO-A-96035711, WO-A-96035712 and WO-A-96035714.

SUMMARY OF THE INVENTION

The invention encompasses compounds which are useful inhibitors of matrix metalloproteinases and/or TNFα-mediated diseases, including degenerative diseases and certain cancers. These compounds are represented by formula (I):

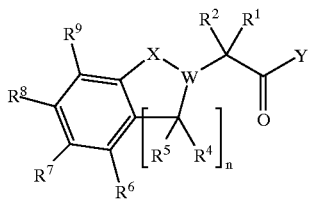

(I)

wherein
n is 1–2;
X is OH or $S(O)_{0-2}$;
Y is OH or NHOH;
W is $CR^3$ or, when X is $SO_2$, W may alternatively be N;
$R^1$ is H or a group selected from $C_{1-6}$ alkyl, $C_{2-6}$ alkenyl, aryl, $C_{1-6}$ alkyl-aryly heteroaryl, $C_{1-6}$ alkyl-heteroaryl, heterocycloalkyl, $C_{1-6}$ alkyl-heterocycloalkyl, cycloalkyl and $C_{1-6}$ alkyl-cycloalkyl, wherein said group is optionally substituted with $R^{14}$, and $R^2$ is H or $C_{1-6}$ alkyl, or
$CR^1R^2$ is a cycloalkyl or heterocycloalkyl ring, optionally substituted with $R^{14}$ or a group (optionally substituted with $R^{14}$) selected from $C_{1-6}$ alkyl, aryl, $C_{1-6}$ alkyl-aryl;
$R^3$, $R^4$ and $R^5$ are independently H or $C_{1-6}$ alkyl or $R^3$ and $R^4$ may together represent a bond such that $CR^3CR^4R^5$ is $C=CR^5$; $R^5$;
$R^6$, $R^7$, $R^8$ and $R^9$ are independently H, $R^{10}$ or a group (optionally substituted with $R^{10}$) selected from $C_{1-6}$ alkyl, aryl, $C_{1-6}$ alkyl-aryl, $C_{1-6}$ alkyl-heteroaryl, heteroaryl and heterocycloalkyl, or
$R^6$ and $R^7$, $R^7$ and $R^8$, $R^8$ and $R^9$, or when n=1, $R^5$ and $R^6$, and the carbons to which they are independently attached may alternatively form an aryl, heteroaryl, cycloalkenyl or heterocycloalkenyl ring, wherein said ring is optionally substituted with $R^{10}$ or $R^{11}$;
$R^{10}$ is $C_{1-6}$ alkyl, halogen, CN, $NO_2$, $N(R^{11})_2$, $OR^{11}$, $COR^{11}$, $CO_2R^{15}$, $CON(R^{11})_2$, $C=NOR^{11}$, $NR^{11}R^{12}$, $S(O)_{0-2}R^{11}$ or $SO_2N(R^{11})_2$;
$R^{11}$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said group is optionally substituted with $R^{13}$, $COR^{13}$, $SO_{0-2}R^{13}$, $CO_2R^{13}$, $OR^{13}$, $CONR^{15}R^{13}$, $NR^{15}R^{13}$, halogen, CN, $SO_2NR^{15}R^{13}$ or $NO_2$, and for each case of $N(R^{11})_2$ the $R^{11}$ groups are the same or different or $N(R^{11})_2$ is heterocycloalkyl optionally substituted with $R^{13}$, $COR^{13}$, $SO_{0-2}R^{13}$, $CO_2R^{13}$, $OR^{13}$, $CONR^{15}R^{13}$, $NR^{15}R^{13}$, halogen, CN, $SO_2NR^{15}R^{13}$ or $NO_2$;
$R^{12}$ is $COR^{11}$, $CON(R^{11})_2$, $CO_2R^{13}$ or $SO_2R^{13}$,
$R^{13}$ is $C_{1-6}$ alkyl, axyl, $C_{1-6}$ alkyl-aryl, heteroaryl or $C_{1-6}$ alkyl-heteroaryl; and
$R^{14}$ is $OR^{11}$, $COR^{11}$, $CO_2R^{15}$, $CON(R^{11})_2$, $NR^{11}R^{12}$, $S(O)_{0-2}R^{13}$, $SO_2N(R^{11})_2$, halogen, CN, $NO_2$ or cycloimidyl (optionally substituted with $R^{15}$);
$R^{15}$ is H or $C_{1-6}$ alkyl;
and salts, solvates, hydrates, N-oxides, protected amino, protected carboxy, and protected hydroxamic acid derivatives thereof.

Compounds of formula (I) are disclosed for the first time as having therapeutic utility. Compounds of formula (I) are new, except those wherein Y is OH, X is $S(O)_{0-2}$ and either $CR^1R^2$ is $CH_2$ or X is $SO_2$ and $R^3$ and $R^4$ together are not a bond.

Combinations of substituents and/or variables are only permissible if such combinations result in stable compounds.

DESCRIPTION OF THE INVENTION

Preferred compounds of the invention are those wherein any one or more of the following apply:
X is $SO_2$;
W is $CR^3$;
n is 1;
$R^1$ is optionally substituted $C_{1-6}$ alkyl, $C_{1-6}$ alkyl-aryl, $C_{1-6}$ alkyl-heteroaryl, or $C_{1-6}$ alkyl-heterocycloalkyl, or $CR^1R^2$ forms the said optionally substituted cycloalkyl or heterocycloalkyl ring;
$R^6$, $R^7$, $R^8$ or $R^9$ is $R^{10}$ or optionally substituted aryl or heteroaryl;

$R^{10}$ is $OR^{11}$, $COR^{11}$ or $C=NOR^{11}$;

$R^{11}$ is optionally substituted aryl, $C_{1-6}$ alkyl, $C_{1-6}$ alkyl-aryl, heteroaryl or $C_{1-6}$ alkyl-heteroaryl; and $R^{14}$ is $CO_2R^2$, $CON(R^{11})_2$, $NR^{11}R^{12}$, $S(O)_{0-2}R^{13}$, $SO_2N(R^{11})_2$, or optionally substituted cycloimidyl.

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof As used in this specification, alone or in combination, the term "$C_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cycloalkyl" refers to a saturated alicyclic moiety having from three to six carbon atoms and which may be optionally benzofused at any available position. This term includes for example cyclopropyl, cyclobutyl, cyclopentyl, cyclohexyl, indanyl and tetrahydronaphthyl.

The term "heterocycloalkyl" refers to a saturated heterocyclic moiety having from three to six carbon atoms and one or more heteroatom from the group N, O, S (or oxidised versions thereof) and which may be optionally benzofused at any available position. This term includes for example azetidinyl, pyrrolidinyl, tetrahydrofuranyl, piperidinyl, indolinyl and tetrahydroquinolinyl.

The term "cycloalkenyl" refers to an alicyclic moiety having from three to six carbon atoms and having in addition one double bond. This term would include for example cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "aryl" refers to an aromatic carbocyclic radical having a single ring or two condensed rings. This term includes, for example phenyl or naphthyl.

The term "heteroaryl" refers to aromatic ring systems of five to ten atoms of which at least one atom is selected from O, N and S, and includes for example furanyl, thiophenyl, pyridyl, indolyl, quinolyl and the like.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "benzofused" refers to the addition of a benzene ring sharing a common bond with the defined ring system.

The term "optionally substituted" means optionally substituted with one or more of the groups specified, at any available position or positions.

The term "halogen" means fluorine, chlorine, bromine or iodine.

The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of an ester such as the methyl, ethyl, benzyl or tert-butyl ester. A hydroxamic acid may be protected as either N or O-substituted derivatives such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^{16}$ where $R^{16}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers may be resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, X, Y and W are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A compounds of formula (I) may be prepared by reaction of a compound of formula (II)

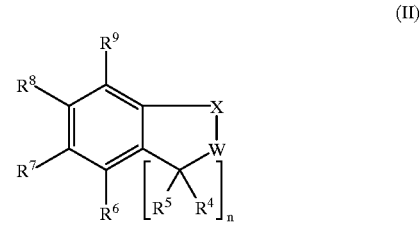

(II)

with compound of formula $Z—CR^1R^2COY$ (III), where Z represents a leaving group such as a halogen, e.g. bromine, or an alkyl or arylsulfonate, e.g. methanesulfonate, under appropriate conditions. Suitable conditions for this reaction are the treatment of compound (II) with strong organic base, such as lithium diisopropylamide in an inert solvent, such as tetrahydrofuran, at an appropriate temperature, such as −78° C., followed by the addition of (III).

Compounds of formula (II) where W=CR³, n=1 and R⁴ is H may be prepared by the hydrogenation (using hydrogen at an appropriate pressure, e.g. 1380 kPa (200 psi), and palladium on carbon in suitable solvent, such as an alcohol, e.g. ethanol) of a compound of formula (IV)

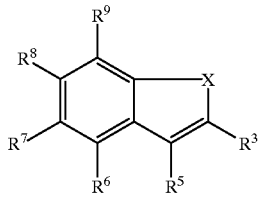

(IV)

Compounds of formula (IV) may be prepared by known methods, e.g. Heterocycles (1974) 21–6; Heterocycles (1987) 2829–34. Compounds of formula (III) may be obtained in chiral or racemic form by methods well known to those skilled in the art, e.g. as described in WO-A-9005719.

Compounds of formula (II) where W=N are known in the literature, and may be prepared as described. For example, see Teeninga et al, J. Org. Chem. (1983) 48:537–542.

Compounds of formula (II) where W=N may alternatively be prepared by ring-closure of a compound of formula (V)

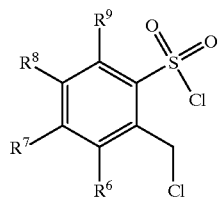

(V)

with ammonia. Alternatively use of an amine in place of ammonia, such as an amine of formula $H_2NCR^1R^2COY$ (VI), may provide compounds of formula (I) directly from (V). For example, see the method described in Rufer et al, Eur. J. Med. Chem. Chem. Ther. (1978) 13:193–198.

Compounds of formula (V) are known in the literature may be prepared as described. For example, see King et al, Can. J. Chem. (1971) 49:943–955.

Compounds of formula (I) or any appropriate intermediate may also be prepared by interconversion of compounds of the same formula. Thus, for example, a compound of formula (I) wherein $R^1$ is a $C_{1-6}$ alkyl group may be prepared by hydrogenation (using palladium on carbon in suitable solvent, such as an alcohol, e.g. ethanol) of a compound of formula (I) wherein $R^1$ is a $C_{2-6}$ alkenyl group. A compound of formula (I) where Y=NHOH may be prepared from a compound where Y=OH using standard chemistry known to those skilled in the art, optionally via the intermediate preparation of hydroxamides $NHOR^{17}$ where $R^{17}$ is a suitable protecting group such as benzyl, tert-butyl or tert-butyldimethylsilyl (TBDMS). Similarly, a compound of formula (I) where X=$SO_2$ may be prepared from a compound of formula (I) where X=S by oxidation with, for example Oxone® in appropriate solvent, such as methanol-water. A compound of formula (I) where $R^1$ is not H may be prepared from a compound of formula (1) where $R^1$ is H by reaction with a compound of formula $ZR^1$ (where Z is as defined above) in the presence of a strong base such as lithium diisopropylamide, in an inert solvent, such as tetrahydrofuran.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysins, collagenases and gelatinases. Compounds according to the invention may also exhibit in vitro inhibition of membrane shedding events known to be mediated by metalloproteinases, for example, TNF release, TNF receptor shedding, IL-6 receptor shedding, IL-1 receptor shedding, CD23 shedding and L-selectin shedding. The activity and selectivity of the compounds may be determined by use of the appropriate enzyme inhibition test, for example as described in Examples A–M of WO 98/05635, or by the following assay for the inhibition of CD23 shedding.

The potency of compounds of general formula (I) to act as inhibitors of the shedding of CD23 is determined using the following procedure: a 100 μM solution of the compound being tested, or dilutions thereof, is incubated at 37° C. in an atmosphere of 5% $CO_2$ with RPMI 8866 cells, which shed CD23 spontaneously without stimulation. After 1 h, the cells are removed by centrifugation and the supernatant assayed for levels of sCD23 using an ELISA kit available commercially. The activity in the presence of 0.1 mM inhibitor, or dilutions thereof, is compared to activity in a control devoid of inhibitor and the results reported as that inhibitor concentration effecting 50% inhibition of the shedding of CD23.

This invention also relates to a method of treatment for patients (including man and/or mammalian animals raised in the dairy, meat or fur industries or as pets) suffering from disorders or diseases which can be attributed to MMPs as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoinmmune diseases cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis and aspirin-independent anti-thrombosis.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinylpyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouth washes and gargles.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

In the Examples, the following abbreviations are used:

| | |
|---|---|
| TNFα | Tumour Necrosis Factor α |
| LPS | Lipopolysaccharide |
| ELISA | Enzyme-linked immunosortbant assay |
| EDC | 1-Ethyl-2-dimethylaminopropylcarbodiimide |
| RT | Room Temperature |

EXAMPLE 1

2-(3-Methyl-1H-benzo[b]thiophen-2-yl)-5-phenylpentanoic Acid

To a stirred solution of 3-methylbenzo[b]thiophene-2-acetic acid (1.00 g) in THF at −78° C. under nitrogen was added a solution of n-butyllithium in hexanes (2.5M; 3.98 ml). Stirring was continued for 15 mins at this temperature before 1-bromo-3-phenylpropane (965 mg) was added. The mixture was stirred for 30 mins before allowing to warm up to RT and then stirred at RT for a further 1 h. The reaction mixture was poured on to a mixture of water (50 ml) and 1 N sodium hydroxide solution (10 ml). The organic layer was separated and washed with water (2×10 ml), brine (10 ml) and dried (MgSO$_4$). Filtration and evaporation of solvents under reduced pressure gaven the crude product, which was purificatied by silica gel column chromatography, eluting with 2:1 hexane/ethyl acetate, to give the title compound (579 mg, 37%) as a pale green oil. R$_f$ 0.45 (2:1 hexane/ethyl acetate).

EXAMPLE 2

2-(3Methyl-1,1-dioxo-1H-benzo[b]thiophen-2-yl)-5-phenyl-pentanoic Acid

To a stirred solution of Example 1 (568 mg) in methanol at RT was added a solution of Oxone® (1.61 g) in water (20 ml). The mixture was stirred for 72 h before being diluted with water (100 ml) and extracted with dichloromethane (4×25 ml). The combined dichloromethane extracts were washed with water (25 ml), brine (25 ml) and dried (MgSO$_4$). Filtration and evaporation of solvents under reduced pressure yielded the title compound (504 mg, 81%) as a white foam. R$_f$ 0.33 (2:1 ethyl acetate/hexane).

EXAMPLE 3

2-(3-Methyl-1,1-dioxo-1H-benzo[b]thiophen-2-yl)-5-phenyl-petanoic Acid N-Hydroxy Amide To a stirred solution of Example 2 (500 mg) in dichloromethane (25 ml) at 0° C. was added EDC (269 mg) and O-tert-butyldimethylsilylhydroxylamine (207 mg). Stirring was continued for 16 h, with the temperature rising to RT before the solution was diluted with dichloromethane (50 ml). The reaction mixture was washed with water (2×25 ml), brine (25 ml) and dried (MgSO$_4$). Filtration and evaporation of solvents under reduced pressure gave a colourless oil that was dissolved in dichloromethane (15 ml) and treated with a solution of hydrogen chloride in diethyl ether (1M; 4.09 ml). The mixture was stirred for 1 h before the solvents were removed in vacuo and the residue was purified by silica gel column chromatography eluting with ethyl acetate to yield the title compound (278 mg, 55%) as a white solid.

R$_f$ 0.40 (3:1 ethyl acetate/hexane).

MS 371 (M$^+$)

EXAMPLE 4

2-(3-Methyl-1,1-dioxo-2,3-dihydro-1H-benzo[b]thiophen-2-yl)-5-phenylpentanoic Acid N-Hydroxy Amide To a stirred solution of Example 3 (120 mg) in ethyl acetate (15 ml) at RT was added palladium on charcoal (10%; 12 mg). Hydrogen gas was introduced and stirring was continued for 8 h. The mixture was filtered and the filtrate was evaporated to dryness to yield the title product (97 mg, 80%) as a white solid.

R$_f$ 0.27 (2:1 ethyl acetate/hexane)

MS 373 (M$^+$)

What is claimed is:

1. A compound, represented by formula (I):

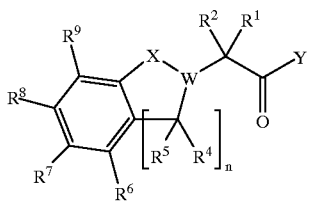

(I)

wherein n is 1–2;

X is O or $S(O)_{0-2}$;

Y is NHOH;

W is $CR^3$ or (when X is $SO_2$) N;

$R^1$ is H or a substituent selected from the group consisting of $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl, and $C_{1-6}$ alkyl-cycloalkyl, wherein said substituent is optionally substituted with $R^{14}$, and $R^2$ is H or $C_{1-6}$ alkyl, or $CR^1R^2$ is a cycloalkyl or heterocycloalkyl ring, optionally substituted with $R^{14}$ or a substituent (optionally substituted with $R^{14}$) selected from the group consisting of $C_{1-6}$ alkyl, aryl, $C_{1-6}$ alkyl-aryl;

$R^3$, $R^4$ and $R^5$ are independently H or $C_{1-6}$ alkyl, or $R^3$ and $R^4$ may together represent a bond;

$R^6$, $R^7$, $R^8$, and $R^9$ are independently H, $R^{10}$, or a group (optionally substituted with $R^{10}$) selected from the group consisting of $C_{1-6}$ alkyl, aryl, $C_{1-6}$ alkyl-aryl, $C_{1-6}$ alkyl-heteroaryl, heteroaryl, and heterocycloalkyl, or $R^6$ and $R^7$, $R^7$ and $R^8$, $R^8$ and $R^9$, or when n=1, $R^5$ and $R^6$, and the carbons to which they are independently attached may alternatively form an aryl, heteroaryl, cycloalkenyl or hetercycloalkenyl ring, wherein said ring is optionally substituted with $R^{10}$ or $R^{11}$;

$R^{10}$ is selected from the group consisting of $C_{1-6}$ alkyl, Br, I, F, CN, $NO_2$, $N(R^{11})_2$, $OR^{11}$, $COR^{11}$, $CO_2R^{15}$, $CON(R^{11})_2$, $C=NOR^{11}$, $NR^{11}R^{12}$, $S(O)_{0-2}R^{11}$, and $SO_2N(R^{11})_2$;

$R^{11}$ is selected from the group consisting of H, $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocyloalkyl, and $C_{1-6}$ alkyl-heterocycloalkyl, wherein said group is optionally substituted with $R^{13}$, $COR^{13}$, $SO_{0-2}R^{13}$, $CO_2R^{13}$, $OR^{13}$, $CONR^{15}R^{13}$, $NR^{15}R^{13}$, halogen, CN, $SO_2NR^{15}R^{13}$ or $NO_2$, and for each case of $N(R^{11})_2$ the $R^{11}$ groups are the same or different or $N(R^{11})_2$ is heterocycloalkyl optionally substituted with a substituent selected from the group consisting of $R^{13}$, $COR^{13}$, $SO_{0-2}R^{13}$, $CO_2R^{13}$, $OR^{13}$, $CONR^{15}R^{13}$, $NR^{15}R^{13}$, halogen, CN, $SO_2R^{15}R^{13}$, and $NO_2$;

$R^{12}$ is selected from the group consisting of $COR^{11}$, $CON(R^{11})_2$, $CO_2R^{13}$, and $SO_2R^{13}$;

$R^{13}$ is selected from the group consisting of $C_{1-6}$ alkyl, aryl, $C_{1-6}$ alkyl-aryl, heteroaryl, and $C_{1-6}$ alkyl-heteroaryl;

$R^{14}$ is selected from the group consisting of $OR^{11}$, $COR^{11}$, $CO_2R^{15}$, $CON(R^{11})_2$, $NR^{11}R^{12}$, $S(O)_{0-2}R^{13}$, $SO_2N(R^{11})_2$, halogen, CN, $NO_2$, and cycloimidyl (optionally substituted with $R^{15}$); and $R^{15}$ is H or $C_{1-6}$ alkyl;

and salts, solvates, hydrates, N-oxides, protected amino, protected carboxy, and protected hydroxamic acid derivatives thereof.

2. The compound, according to claim 1, wherein X is $SO_2$.

3. The compound, according to claim 1, wherein $R^{14}$ is selected from the group consisting of $CO_2R^2$, $CON(R^{11})_2$, $NR^{11}R^{12}$, $S(O)_{0-2}R^{13}$, $SO_2N(R^{11})_2$, and optionally substituted cycloimidyl.

4. The compound, according to claim 1, wherein $R^1$ is selected from the group consisting of optionally substituted $C_{1-6}$ alkyl, $C_{1-6}$ alkyl-aryl, $C_{1-6}$ alkyl-heteroaryl, and $C_{1-6}$ alkyl-heterocycloalkyl.

5. The compound, according to claim 1, wherein $CR^1R^2$ forms the said optionally substituted cycloalkyl or heterocycloalkyl ring.

6. The compound, according to claim 1, wherein any or all of $R^6$, $R^7$, $R^8$ and $R^9$ are $R^{10}$ or optionally substituted aryl or heteroaryl, $R^{10}$ is $OR^{11}$ or $COR^{11}$, $R^{11}$ is selected from the group consisting of optionally substituted aryl, alkyl, $C_{1-6}$ alkyl-aryl, heteroaryl, and $C_{1-6}$ alkyl-heteroaryl.

7. The compound, according to claim 1, selected from the group consisting of 2-(3-methyl-1,1-dioxo-1H-benzo[b]thiophen-2-yl)-5-phenylpentanoic acid N-hydroxy amide, and 2-(3-methyl-1,1-dioxo-2,3-dihydro-1H-benzo[b]thiophen-2-yl)-5-phenylpentanoic acid N-hydroxy amide.

8. The compound, according to claim 1, in the form of a single enantiomer or diastereomer.

9. A pharmaceutical composition, comprising a compound of claim 1, and a pharmaceutically-acceptable diluent or carrier.

10. A method for the treatment of a condition associated with matrix metalloproteinases or that is mediated by TNFα or enzymes involved in the shedding of L-selectin, CD23, the TNF receptors, IL-6 receptors, or IL-1 receptors, wherein said method comprises administration of an effective amount of a composition comprising a compound represented by formula (I):

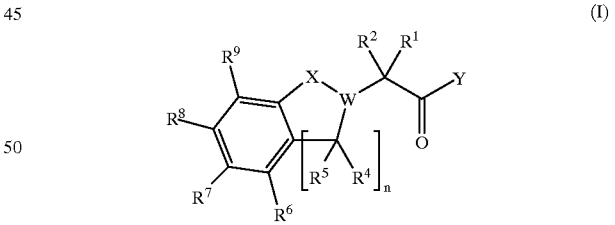

(I)

wherein n is 1–2;

X is O or $S(O)_{1-2}$;

Y is OH or NHOH;

W is $CR^3$ or (when X is $SO_2$) N;

$R^1$ is H or a substituent selected from the group consisting of $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl, and $C_{1-6}$ alkyl-cycloalkyl, wherein said substitutent is optionally substituted with $R^{14}$, $R^2$ is H or $C_{1-6}$ alkyl, or CR$^1$R$^2$ is a cycloalkyl or heterocycloalkyl ring, optionally substituted with R$^{14}$ or a substituent (optionally substituted with R$^{14}$) selected from the group consisting of C$_{1-6}$ alkyl, aryl, C$_{1-6}$ alkyl-aryl;

R$^3$, R$^4$ and R$^5$ are independently H or C$_{1-6}$ alkyl, or R$^3$ and R$^4$ may together represent a bond;

R$^6$, R$^7$, R$^8$, and R$^9$ are independently H, R$^{10}$, or a group (optionally substituted with R$^{10}$) selected from the group consisting of C$_{1-6}$ alkyl, aryl, C$_{1-6}$ alkyl-aryl, C$_{1-6}$ alkyl-heteroaryl, heteroaryl, and heterocycloalkyl, or R$^6$ and R$^7$, R$^7$ and R$^8$, R$^8$ and R$^9$, or when n=1, R$^5$ and R$^6$, and the carbons to which they are independently attached may alternatively form an aryl, heteroaryl, cycloalkenyl or hetercycloalkenyl ring, wherein said ring is optionally substituted with R$^{10}$ or R$^{11}$;

R$^{10}$ is selected from the group consisting of C$_{1-6}$ alkyl, halogen, CN, NO$_2$, N(R$^{11}$)$_2$, OR$^{11}$, COR$^{11}$, CO$_2$R$^{15}$, CON(R$^{11}$)$_2$, C=NOR$^{11}$, NR$^{11}$R$^{12}$, S(O)$_{0-2}$R$^{11}$, and SO$_2$N(R$^{11}$)$_2$;

R$^{11}$ is selected from the group consisting of H, C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocyloalkyl, and C$_{1-6}$ alkyl-heterocycloalkyl, wherein said group is optionally substituted with R$^{13}$, COR$^{13}$, SO$_{0-2}$R$^{13}$, CO$_2$R$^{13}$, OR$^{13}$, CONR$^{15}$R$^{13}$, NR$^{15}$R$^{13}$, halogen, CN, SO$_2$NR$^{15}$R$^{13}$ or NO$_2$, and for each case of N(R$^{11}$)$_2$ the R$^{11}$ groups are the same or different or N(R$^{11}$)$_2$ is heterocycloalkyl optionally substituted with a substituent selected from the group consisting of R$^{13}$, COR$^{13}$, SO$_{0-2}$R$^{13}$, CO$_2$R$^{13}$, OR$^{13}$, CONR$^{15}$R$^{13}$, NR$^{15}$R$^{13}$, halogen, CN, SO$_2$R$^{15}$R$^{13}$, and NO$_2$;

R$^{12}$ is selected from the group consisting of COR$^{11}$, CON(R$^{11}$)$_2$, CO$_2$R$^{13}$, and SO$_2$R$^{13}$;

R$^{13}$ is selected from the group consisting of C$_{1-6}$ alkyl, aryl, C$_{1-6}$ alkyl-aryl, heteroaryl, and C$_{1-6}$ alkyl-heteroaryl;

R$^{14}$ is selected from the group consisting of OR$^{11}$, COR$^{11}$, CO$_2$R$^{15}$, CON(R$^{11}$)$_2$, NR$^{11}$R$^{12}$, S(O)$_{0-2}$R$^{13}$, SO$_2$N(R$^{11}$)$_2$, halogen, CN, NO$_2$, and cycloimidyl (optionally substituted with R$^{15}$); and R$^{15}$ is H or C$_{1-6}$ alkyl;

and salts, solvates, hydrates, N-oxides, protected amino, protected carboxy, and protected hydroxamic acid derivatives thereof.

11. The method, according to claim 10, wherein said condition is selected from the group consisting of cancer, inflammation and inflammatory diseases, tissue degeneration, periodontal disease, ophthalmological disease, dermatological disorders, fever, cardiovascular effects, haemorrhage, coagulation and acute phase response, cachexia, anorexia, acute infection, HIV infection, shock states, graft versus host reactions, autoimmune disease, reperfusion injury, meningitis, migraine, and aspirin-independent anti-thrombosis.

12. The method, according to claim 10, wherein said condition is selected from the group consisting of tumor growth, angiogenesis, tumor invasion and spread, metastases, malignant ascites, and malignant pleural effusion.

13. The method, according to claim 10, wherein said condition is selected from the group consisting of cerebral ischaemia, ischaemic heart disease, rheumatoid arthritis, osteoarthritis, osteoporosis, asthma, multiple sclerosis, neurodegeneration, Alzheimer's, atherosclerosis, stroke, vasculitis, Crohn's disease, and ulcerative colitis.

14. The method, according to claim 10, wherein said condition is selected from the group consisting of corneal ulceration, retinopathy, and surgical wound healing.

15. The method, according to claim 10, wherein said condition is selected from the group consisting of psoriasis, atopic dermatitis, chronic ulcers, and epidermolysis bullosa.

16. The method, according to claim 10, wherein said condition is selected from the group consisting of periodontitis and gingivitis.

17. The method, according to claim 10, wherein said condition is selected from the group consisting of rhinitis, allergic conjunctivitis, eczema, and anaphylaxis.

18. The method, according to claim 10, wherein said condition is selected from the group consisting of restenosis, congestive heart failure, endometriosis, atherosclerosis, and endosclerosis.

19. The method, according to claim 10, wherein said condition is selected from the group consisting of pelvic inflammatory disease (PID), age-related muscular degeneration, and cancer-induced bone resorption.

20. The method, according to claim 10, wherein said condition is a lung disease.

21. The method, according to claim 10, wherein said condition is selected from the group consisting of cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulomatosis, pulmonary lymphangioleiomyomatosis (LAM), and chronic obstructive pulmonary disease (COPD).

22. The method, according to claim 10, wherein when Y is OH and X is S(O)$_{0-2}$, CR$^1$R$^2$ is not CH$_2$ and/or R$^3$ and R$^4$ can only represent a bond when X is not SO$_2$.

23. The method, according to claim 10, wherein Y is NHOH.

24. The method, according to claim 10, wherein X is SO$_2$.

25. The method, according to claim 10, wherein R$^{14}$ is selected from the group consisting of CO$_2$R$^2$, CON(R$^{11}$)$_2$, NR$^{11}$R$^{12}$, S(O)$_{0-2}$R$^{13}$, SO$_2$N(R$^{11}$)$_2$, and optionally substituted cycloimidyl.

26. The method, according to claim 10, wherein R$^1$ is selected from the group consisting of optionally substituted C$_{1-6}$ alkyl, C$_{1-6}$ alkyl-aryl, C$_{1-6}$ alkyl-heteroaryl, and C$_{1-6}$ alkyl-heterocycloalkyl.

27. The method, according to claim 10, wherein CR$^1$R$^2$ forms the said optionally substituted cycloalkyl or heterocycloalkyl ring.

28. The method, according to claim 10, wherein any or all of R$^6$, R$^7$, R$^8$ and R$^9$ are R$^{10}$ or optionally substituted aryl or heteroaryl, R$^{10}$ is OR$^{11}$ or COR$^{11}$, R$^{11}$ is selected from the group consisting of optionally substituted aryl, alkyl, C$_{1-6}$ alkyl-aryl, heteroaryl, and C$_{1-6}$ alkyl-heteroaryl.

29. The method, according to claim 10, wherein said compound is selected from the group consisting of 2-(3-methyl-1,1-dioxo-1H-benzo[b]thiophen-2-yl)-5-phenylpentanoic acid, 2-(3-methyl-1,1-dioxo-1H-benzo[b]thiophen-2-yl)-5-phenylpentanoic acid N-hydrodoxy amide, and 2-(3-methyl-1,1-dioxo-2,3-dihydro-1H-benzo[b]thiophen-2-yl-5-phenylpentanoic acid N-hydroxy amide.

30. The method, according to claim 10, wherein said compound is in the form of a single enantiomer or diastereomer.

31. The compound of claim 1, wherein W is CR$^3$.

32. The method of claim 10, wherein W is CR$^3$.

33. A compound, represented by formula (I):

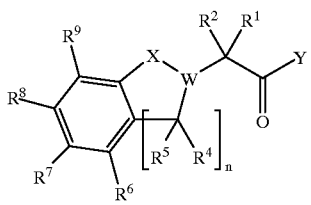

wherein
n is 1–2;
X is O or $S(O)_{1-2}$;
Y is NHOH;
W is $CR^3$ or (when X is $SO_2$) N;
$R^1$ is H or a substituent selected from the group consisting of $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl, and $C_{1-6}$ alkyl-cycloalkyl, wherein said substituent is optionally substituted with $R^{14}$, and
$R^2$ is H or $C_{1-6}$ alkyl, or
$CR^1R^2$ is a cycloalkyl or heterocycloalkyl ring, optionally substituted with $R^{14}$ or a substituent (optionally substituted with $R^{14}$) selected from the group consisting of $C_{1-6}$ alkyl, aryl, $C_{1-6}$ alkyl-aryl;
$R^3$, $R^4$ and $R^5$ are independently H or $C_{1-6}$ alkyl, or $R^3$ and $R^4$ may together represent a bond;
$R^6$, $R^7$, $R^8$, and $R^9$ are independently H, $R^{10}$, or a group (optionally substituted with $R^{10}$) selected from the group consisting of $C_{1-6}$ alkyl, aryl, $C_{1-6}$ alkyl-aryl, $C_{1-6}$ alkyl-heteroaryl, heteroaryl, and heterocycloalkyl, or
$R^6$ and $R^7$, $R^7$ and $R^8$, $R^8$ and $R^9$, or when n=1, $R^5$ and $R^6$, and the carbons to which they are independently attached may alternatively form an aryl, heteroaryl, cycloalkenyl or hetercycloalkenyl ring, wherein said ring is optionally substituted with $R^{10}$ or $R^{11}$;
$R^{10}$ is selected from the group consisting of $C_{1-6}$ alkyl, halogen, CN, $NO_2$, $N(R^{11})_2$, $OR^{11}$, $COR^{11}$, $CO_2R^{15}$, $CON(R^{11})_2$, $C=NOR^{11}$, $NR^{11}R^{12}$, $S(O)_{0-2}R^{11}$, and $SO_2N(R^{11})_2$;
$R^{11}$ is selected from the group consisting of H, $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocyloalkyl, and $C_{1-6}$ alkyl-heterocycloalkyl, wherein said group is optionally substituted with $R^{13}$, $COR^{13}$, $SO_{0-2}R^{13}$, $CO_2R^{13}$, $OR^{13}$, $CONR^{15}R^{13}$, $NR^{15}R^{13}$, halogen, CN, $SO_2NR^{15}R^{13}$ or $NO_2$, and for each case of $N(R^{11})_2$ the $R^{11}$ groups are the same or different or $N(R^{11})_2$ is heterocycloalkyl optionally substituted with a substituent selected from the group consisting of $R^{13}$, $COR^{13}$, $SO_{0-2}R^{13}$, $CO_2R^{13}$, $OR^{13}$, $CONR^{15}R^{13}$, $NR^{15}R^{13}$, halogen, CN, $SO_2R^{15}R^{13}$, and $NO_2$;
$R^{12}$ is selected from the group consisting of $COR^{11}$, $CON(R^{11})_2$, $CO_2R^{13}$, and $SO_2R^{13}$;
$R^{13}$ is selected from the group consisting of $C_{1-6}$ alkyl, aryl, $C_{1-6}$ alkyl-aryl, heteroaryl, and $C_{1-6}$ alkyl-heteroaryl;
$R^{14}$ is selected from the group consisting of $OR^{11}$, $COR^{11}$, $CO_2R^{15}$, $CON(R^{11})_2$, $NR^{11}R^{12}$, $S(O)_{0-2}R^{13}$, $SO_2N(R^{11})_2$, halogen, CN, $NO_2$, and cycloimidyl (optionally substituted with $R^{15}$); and $R^{15}$ is H or $C_{1-6}$ alkyl;
and salts, solvates, hydrates, N-oxides, protected amino, protected carboxy, and protected hydroxamic acid derivatives thereof.

34. The compound, according to claim 33, wherein X is $SO_2$.

35. The compound, according to claim 33, wherein $R^{14}$ is selected from the group consisting of $CO_2R^2$, $CON(R^{11})_2$, $NR^{11}R^{12}$, $S(O)_{0-2}R^{13}$, $SO_2N(R^{11})_2$, and optionally substituted cycloimidyl.

36. The compound, according to claim 33, wherein $R^1$ is selected from the group consisting of optionally substituted $C_{1-6}$ alkyl, $C_{1-6}$ alkyl-aryl, $C_{1-6}$ alkyl-heteroaryl, and $C_{1-6}$ alkyl-heterocycloalkyl.

37. The compound, according to claim 33, wherein $CR^1R^2$ forms the said optionally substituted cycloalkyl or heterocycloalkyl ring.

38. The compound, according to claim 33, wherein any or all of $R^6$, $R^7$, $R^8$ and $R^9$ are $R^{10}$ or optionally substituted aryl or heteroaryl, $R^{10}$ is $OR^{11}$ or $COR^{11}$, $R^{11}$ is selected from the group consisting of optionally substituted aryl, alkyl, $C_{1-6}$ alkyl-aryl, heteroaryl, and $C_{1-6}$ alkyl-heteroaryl.

39. The compound, according to claim 33, in the form of a single enantiomer or diastereomer.

40. A pharmaceutical composition, comprising a compound of claim 33, and a pharmaceutically-acceptable diluent or carrier.

41. The compound of claim 33, wherein W is $CR^3$.

42. A method for the treatment of a condition associated with matrix metalloproteinases or that is mediated by TNFα or enzymes involved in the shedding of L-selectin, CD23, the TNF receptors, IL-6 receptors, or IL-1 receptors, wherein said method comprises administration of an effective amount of a composition comprising a compound represented by formula (I):

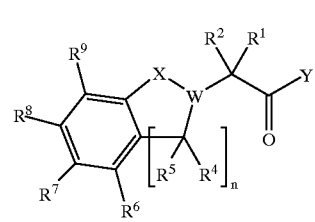

wherein
n is 1–2;
X is O or $S(O)_{0-2}$;
Y is NHOH;
W is $CR^3$ or (when X is $SO_2$) N;
$R^1$ is H or a substituent selected from the group consisting of $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl, and $C_{1-6}$ alkyl-cycloalkyl, wherein said substituent is optionally substituted with $R^{14}$,
$R^2$ is H or $C_{1-6}$ alkyl, or
$CR^1R^2$ is a cycloalkyl or heterocycloalkyl ring, optionally substituted with $R^{14}$ or a substituent (optionally substituted with $R^{14}$) selected from the group consisting of $C_{1-6}$ alkyl, aryl, $C_{1-6}$ alkyl-aryl;
$R^3$, $R^4$ and $R^5$ are independently H or $C_{1-6}$ alkyl, or $R^3$ and $R^4$ may together represent a bond;
$R^6$, $R^7$, $R^8$, and $R^9$ are independently H, $R^{10}$, or a group (optionally substituted with $R^{10}$) selected from the group consisting of $C_{1-6}$ alkyl, aryl, $C_{1-6}$ alkyl-aryl, $C_{1-6}$ alkyl-heteroaryl, heteroaryl, and heterocycloalkyl, or $R^6$ and $R^7$, $R^7$ and $R^8$, $R^8$ and $R^9$, or when n=1, $R^5$ and $R^6$, and the carbons to which they are independently attached may alternatively form an aryl, heteroaryl, cycloalkenyl or hetercycloalkenyl ring, wherein said ring is optionally substituted with $R^{10}$ or $R^{11}$;

$R^{10}$ is selected from the group consisting of $C_{1-6}$ alkyl, Br, I, F, CN, $NO_2$, $N(R^{11})_2$, $OR^{11}$, $COR^{11}$, $CO_2R^{15}$, $CON(R^{11})_2$, $C=NOR^{11}$, $NR^{11}R^{12}$, $S(O)_{0-2}R^{11}$, and $SO_2N(R^{11})_2$;

$R^{11}$ is selected from the group consisting of H, $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocyloalkyl, and $C_{1-6}$ alkyl-heterocycloalkyl, wherein said group is optionally substituted with $R^{13}$, $COR^{13}$, $SO_{0-2}R^{13}$, $CO_2R^{13}$, $OR^{13}$, $CONR^{15}R^{13}$, $NR^{15}R^{13}$, halogen, CN, $SO_2NR^{15}R^{13}$ or $NO_2$, and for each case of $N(R^{11})_2$ the $R^{11}$ groups are the same or different or $N(R^{11})_2$ is heterocycloalkyl optionally substituted with a substituent selected from the group consisting of $R^{13}$, $COR^{13}$, $SO_{0-2}R^{13}$, $CO_2R^{13}$, $OR^{13}$, $CONR^{15}R^{13}$, $NR^{15}R^{13}$, halogen, CN, $SO_2R^{15}R^{13}$, and $NO_2$;

$R^{12}$ is selected from the group consisting of $COR^{11}$, $CON(R^{11})_2$, $CO_2R^{13}$, and $SO_2R^{13}$;

$R^{13}$ is selected from the group consisting of $C_{1-6}$ alkyl, aryl, $C_{1-6}$ alkyl-aryl, heteroaryl, and $C_{1-6}$ alkyl-heteroaryl;

$R^{14}$ is selected from the group consisting of $OR^{11}$, $COR^{11}$, $CO_2R^{15}$, $CON(R^{11})_2$, $NR^{11}R^{12}$, $S(O)_{0-2}R^{13}$, $SO_2N(R^{11})_2$, halogen, CN, $NO_2$, and cycloimidyl (optionally substituted with $R^{15}$); and $R^{15}$ is H or $C_{1-6}$ alkyl;

and salts, solvates, hydrates, N-oxides, protected amino, protected carboxy, and protected hydroxamic acid derivatives thereof.

43. The method, according to claim 42, wherein said condition is selected from the group consisting of cancer, inflammation and inflammatory diseases, tissue degeneration, periodontal disease, ophthalmological disease, dermatological disorders, fever, cardiovascular effects, haemorrhage, coagulation and acute phase response, cachexia, anorexia, acute infection, HIV infection, shock states, graft versus host reactions, autoimmune disease, reperfusion injury, meningitis, migraine, and aspirin-independent anti-thrombosis.

44. The method, according to claim 42, wherein said condition is selected from the group consisting of tumor growth, angiogenesis, tumor invasion and spread, metastases, malignant ascites, and malignant pleural effusion.

45. The method, according to claim 42, wherein said condition is selected from the group consisting of cerebral ischaemia, ischaemic heart disease, rheumatoid arthritis, osteoarthritis, osteoporosis, asthma, multiple sclerosis, neurodegeneration, Alzheimer's, atherosclerosis, stroke, vasculitis, Crohn's disease, and ulcerative colitis.

46. The method, according to claim 42, wherein said condition is selected from the group consisting of corneal ulceration, retinopathy, and surgical wound healing.

47. The method, according to claim 42, wherein said condition is selected from the group consisting of psoriasis, atopic dermatitis, chronic ulcers, and epidermolysis bullosa.

48. The method, according to claim 42, wherein said condition is selected from the group consisting of periodontitis and gingivitis.

49. The method, according to claim 42, wherein said condition is selected from the group consisting of rhinitis, allergic conjunctivitis, eczema, and anaphylaxis.

50. The method, according to claim 42, wherein said condition is selected from the group consisting of restenosis, congestive heart failure, endometriosis, atherosclerosis, and endosclerosis.

51. The method, according to claim 42, wherein said condition is selected from the group consisting of pelvic inflammatory disease (PID), age-related muscular degeneration, and cancer-induced bone resorption.

52. The method, according to claim 42, wherein said condition is a lung disease.

53. The method, according to claim 52, wherein said condition is selected from the group consisting of cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulomatosis, pulmonary lymphangioleiomyomatosis (LAM), and chronic obstructive pulmonary disease (COPD).

54. The method, according to claim 42, wherein X is $SO_2$.

55. The method, according to claim 42, wherein $R^{14}$ is selected from the group consisting of $CO_2R^2$, $CON(R^{11})_2$, $NR^{11}R^{12}$, $S(O)_{0-2}R^{13}$, $SO_2N(R^{11})_2$, and optionally substituted cycloimidyl.

56. The method, according to claim 42, wherein $R^1$ is selected from the group consisting of optionally substituted $C_{1-6}$ alkyl, $C_{1-6}$alkyl-aryl, $C_{1-6}$ alkyl-heteroaryl, and $C_{1-6}$ alkyl-heterocycloalkyl.

57. The method, according to claim 42, wherein $CR^1R^2$ forms the said optionally substituted cycloalkyl or heterocycloalkyl ring.

58. The method, according to claim 42, wherein any or all of $R^6$, $R^7$, $R^8$ and $R^9$ are $R^{10}$ or optionally substituted aryl or heteroaryl, $R^{10}$ is $OR^{11}$ or $COR^{11}$, $R^{11}$ is selected from the group consisting of optionally substituted aryl, alkyl, $C_{1-6}$ alkyl-aryl, heteroaryl, and $C_{1-6}$ alkyl-heteroaryl.

59. The method, according to claim 42, wherein said compound is in the form of a single enantiomer or diastereomer.

60. The method of claim 42, wherein W is $CR^3$.

* * * * *

UNITED STATES PATENT AND TRADEMARK OFFICE
CERTIFICATE OF CORRECTION

PATENT NO. : 6,310,088 B1
DATED : October 30, 2001
INVENTOR(S) : Andrew Douglas Baxter et al.

It is certified that error appears in the above-identified patent and that said Letters Patent is hereby corrected as shown below:

<u>Column 12,</u>
Line 65, "substitutent" should read -- substituent --.

<u>Column 14,</u>
Line 24, "claim 10," should read -- claim 20, --.
Line 59, "N-hydrodoxy amide," should read -- N-hydroxy amide, --.
Line 61, "thiophen-2-yl-5-phenylpentanoic" should read -- thiophen-2-yl)-5-phenylpentanoic --.

Signed and Sealed this

Thirteenth Day of August, 2002

Attest:

Attesting Officer

JAMES E. ROGAN
Director of the United States Patent and Trademark Office